United States Patent
Wright

[11] Patent Number: 5,659,932
[45] Date of Patent: Aug. 26, 1997

[54] BURIAL CAPSULE WITH ANTI-DECAY SYSTEM

[76] Inventor: George W. Wright, 8600 Belmont Park Dr., Theodore, Ala. 36582

[21] Appl. No.: 641,105

[22] Filed: Apr. 29, 1996

Related U.S. Application Data

[63] Continuation of Ser. No. 392,264, Feb. 22, 1995, abandoned.

[51] Int. Cl.$^6$ .................................................. A61G 17/00
[52] U.S. Cl. .......................................................... 27/7; 27/17
[58] Field of Search .................................. 27/2, 6, 7, 35, 27/123.1, 17

[56] References Cited

U.S. PATENT DOCUMENTS

| | | | |
|---|---|---|---|
| 2,516,488 | 7/1950 | Smith | 27/11 |
| 2,579,756 | 12/1951 | Reed | 27/7 |
| 2,811,768 | 11/1957 | Axelson | 27/7 |
| 3,435,494 | 4/1969 | Pothier | 27/11 |
| 3,681,820 | 8/1972 | Jalbert | 27/7 |
| 3,898,718 | 8/1975 | Eubank | 27/35 |
| 4,924,565 | 5/1990 | Rathjen | 27/11 X |
| 5,222,281 | 6/1993 | Guerin | 27/7 |

FOREIGN PATENT DOCUMENTS 17056 of 1910 United Kingdom.

*Primary Examiner*—Kien T. Nguyen
*Attorney, Agent, or Firm*—George W. Wright, Pro Se

[57] ABSTRACT

Burial capsule with an internal inert gas atmosphere for use to contain the human corpse, or other valuable items, and to protect such items from decay and/or decomposition for an infinite period of time. The burial capsule comprises a one (1) piece elongated, cylindrically shaped enclosure, accomplished by chemically welding two (2) identically configured, homogeneous plastic parts together along a common interfacing surface area. The enclosure contains a single, minute aperture at each opposing end, into which a compatible plastic material female reducer means is chemically welded. A plastic hose adapter is temporarily installed into each reducer; a remote vacuum pump is attached to one (1) adapter, and a remote inert gas means is temporarily attached to the other adapter. The simultaneous activation of the pump and gas means effectively evacuates essentially all of the contaminated gases, and injects an oxygen free, inert gas, environment directly into the confines of the burial capsule. The systematic removal of first the vacuum means, immediately followed by the prompt chemical weldment of a male plug closure means into the reducer means void, and then the removal of the inert gas means, followed by the prompt chemical weldment of a male plug into the other reducer means void, produces a burial capsule which consists of only one (1) homogeneous material part. The hermetically sealed, inert gas filled, one (1) part burial capsule, will effectively protect all items deposited therein from the ravages of decay and/or decomposition indefinitely.

3 Claims, 2 Drawing Sheets

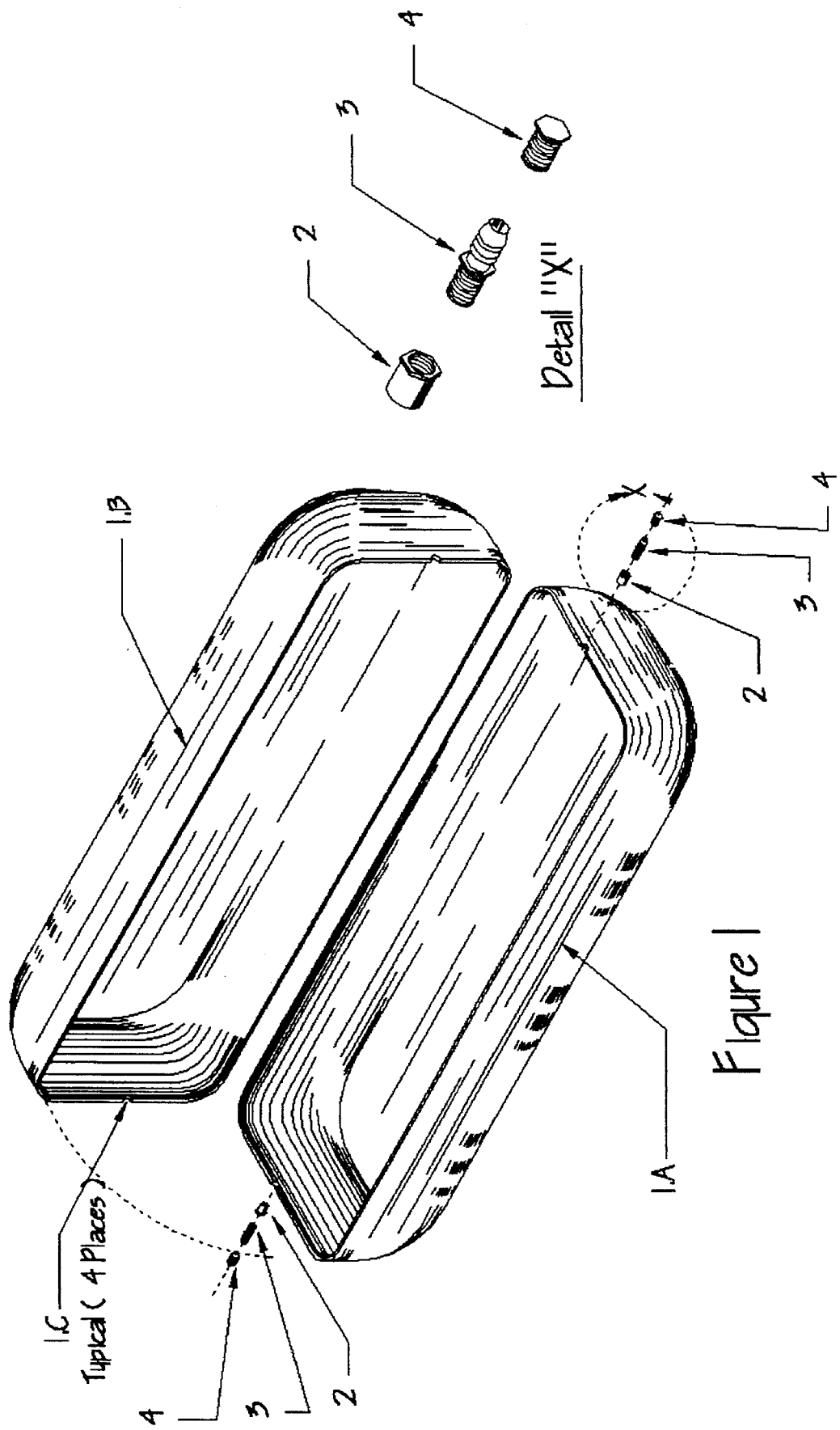

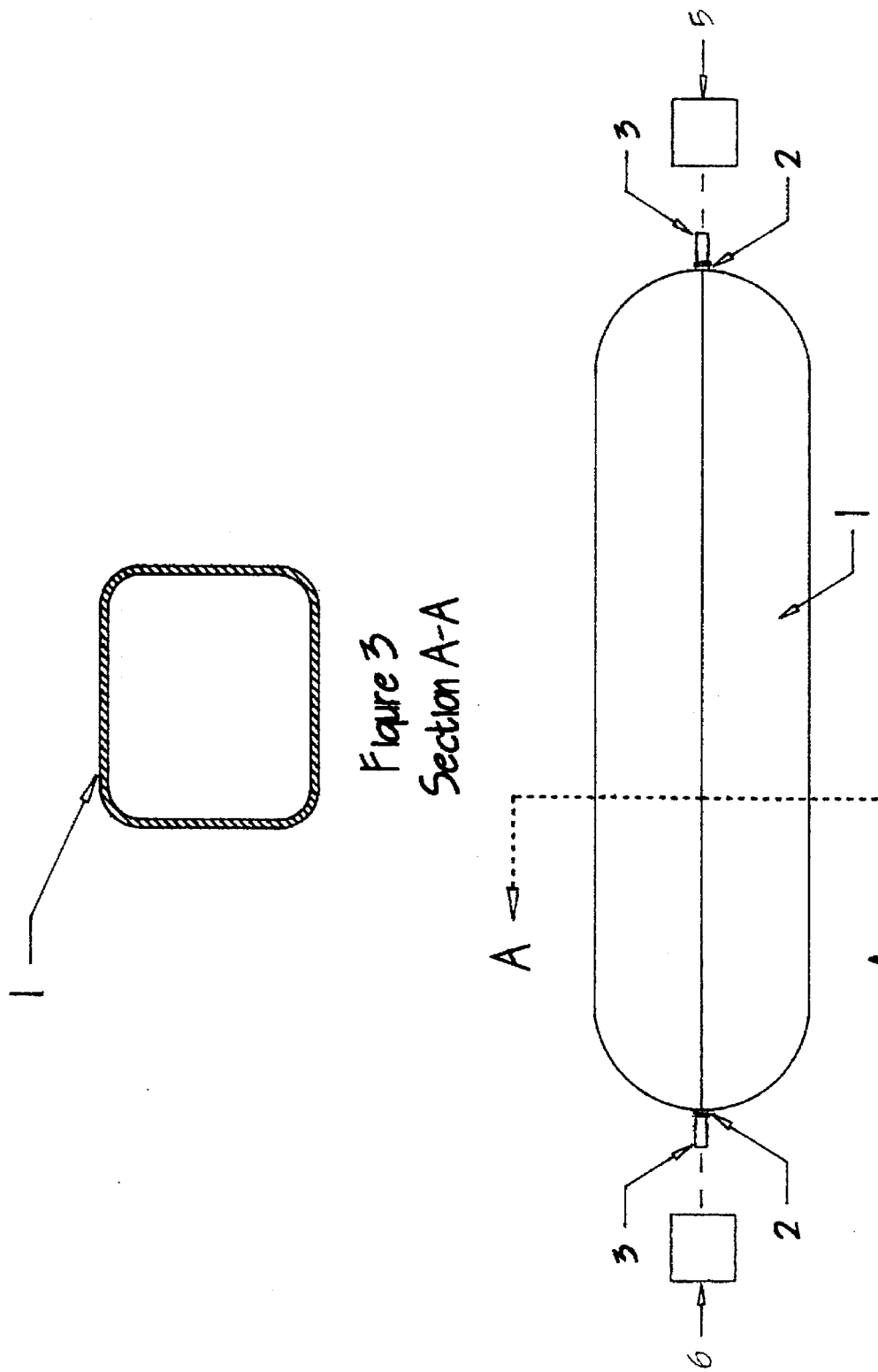

BURIAL CAPSULE WITH ANTI-DECAY SYSTEM

This application is a continuation of patent application Ser. No. 08/392,264 filed on Feb. 22, 1995 now abandoned.

BACKGROUND—CROSS REFERENCE TO RELATED APPLICATIONS

This application is an updated and revised instrument related to prior application Ser. No. 503,732, dated 1983, Jun. 13.

BACKGROUND—FIELD OF THE INVENTION

This invention relates to coffins, vaults, and similar types of containers used for the repository of the human corpse, pet animal remains and/or ultra-valuable items, and most specifically to a burial capsule which will retard the effects of decay and decomposition for up to 100 or more years.

BACKGROUND—DESCRIPTION OF PRIOR ART

Since the beginning of time men have endeavored to design and construct a repository, such as coffins and vaults, wherein the bodies of their deceased loved ones would be preserved and protected from the ravages of decay and decomposition forever. That ultimate goal has never been attained. To the contrary, it is an established fact that all human and/or animal corpses commence to decay and decompose immediately after death occurs.

A recently published German newspaper article clearly attests to this corpse decay factor, and also provides data pertaining to the approximate rate of that decomposition. This item was published by the Deutsche Presse Agentur News Agency in March, 1994. It was re-published in the Mobile Press Register newspaper on Nov. 5, 1994. This article states, in its entirety, as follows:

"The Deutsche Presse Agentur News Agency reported in March that German cemetery operators are worried about the increasing resilience of embalmed bodies. Because of the country's land shortage, burial plots are often only rented out for 15 year periods, with the hope that the bodies will have decomposed by that time, and that families will not object to their disposal. Cemetery owners are now avoiding certain soils that retard air and moisture circulation, for they restrict the growth of bacteria that eat the bodies."

Prior art coffins do not provide any significant protection from decay and decomposition. Most of the available units are very ornate and extremely expensive. There are no coffins in todays marketplace, i.e., Funeral Homes and Mortuaries, which have been specifically designed and/or constructed to provide long time protection of the corpse. This fact has caused extreme distress, and/or serious psychological problems, to untold thousands of family member survivors throughout the entire world.

Several prior art coffins have been patented wherein the inventors have claimed that their coffin/casket was "air tight" or "gas tight". Each such invention typically described an extremely complicated, albeit impossible to attain method for the mating and sealing of two (2) or more segments. Each of these units also required an intricate set of complex valves for the cited purposes of withdrawing air from within the sealed coffin, and the injection of some type of unidentified gas thereinto. All of these types of coffins/caskets have been proven to be totally inadequate and ineffective, as evidenced by their complete absence from within todays marketplace.

Smith (U.S. Pat. No. 2,516,488) teaches a casket which requires two (2) each complex valves (FIGS. 8 and 9) be mounted, in a through-wall manner, onto his casket. Smith further requires that the casket body member 1 be covered with a lid 4, with an "asbestos or other gasket 5" being interposed between said lid and body, and that the lid be secured to the casket body by means of twenty-two (22) each bolts 12. (FIG. 1) The total failure of Smith's teaching is abundantly clear by the fact that said gasket material would have to be approximately sixteen (16) feet long to extend around the circumference distance of said casket. Whereas, the introduction of just one (1) single, infinite size cut, nick, break, or any other type of discontinuity within said gasket material, would ultimately result in the total loss of his required internal protective atmosphere. The probability that such a discontinuity will occur under the given parameters is clearly astronomical, and/or inevitable.

Eubanks (U.S. Pat. No. 3,898,718) teaches "a corpse container 15 comprising a high density outer skin 47 that is unitary with a foamed interior—being sealable about a corpse—and extending to meet and mate with the opposite half—to seal said corpse container." (claim 1.e) Therewith, Eubanks clearly cites his intentions that the corpse become an integral part within the unitary, i.e., indivisible whole, of the corpse container 15 and the foamed plastic 49 within the outer skin 47. Eubanks reveals his intentions very clearly in his FIGS. 4 and 5. As is clearly evidenced therein, the interior of his corpse container is filled to capacity with the described enclosed materials. By virtue thereof, it is abundantly clear that there is no space whatever available within his corpse container for either a gaseous material, nor for any type of valve mechanism type of device.

Jalbert (U.S. Pat. No. 3,681,820) teaches "a burial system for vertically burying—of human remains—including a unique frusto-conical, completely sealed casket made of plastic." The casket 6 includes a frusto-conical hollow body 70, with the large diameter, or "head end" of the casket body to be closed by means of a "circular cap 98", and the smaller diameter end to be closed by an "end cap 114." The corpse bearing casket 6 is required to be inserted into a prepared frusto-conical chamber 4, located within a burial vault 2, which was previously installed in a selected cemetery burial plot. Conspicuously absent from this invention is any type of provision for (1) either the evacuation of entrapped gasses from within the casket, or (2) the introduction of any type of protective atmosphere thereinto, after sealing of said caskets.

As illustrated above, it is exceedingly clear that it would not be obvious, nor physically possible for anyone skilled in the art to utilize the valves taught by Smith, or by any other inventor, within the confines of the coffin taught by Eubanks. These prior art references do not contain any suggestion, either express or implied, that they may be combined in any manner whatever.

Some inventions patented in foreign countries have also taught similar types of un-workable and unsuccessful ideas pertaining to coffins. Becker (England—No. 17,056—A.D. 1910) taught a coffin "provided with a bottle of preservative in order that decomposition of the corpse may be arrested." His teaching was to merely insert a small vial, of some unidentified type of chemical compound, within his coffin. He did not cite any concern nor procedure for the removal of any of the critical, decay causing atmospheric elements trapped therein.

Pothier (France—No. 3,435,494) taught a coffin "constructed of metal designed to reduce or eliminate the evolution of decomposition gasses and, on the other hand, to permit the evacuation of gasses of this type which may be evolved in spite of the arrangements made." He appears to have copied the Becker idea, and placed therein—"a closed cartridge, containing a substance which is capable of giving off a gas, other than oxygen, and means operable from the exterior, for initiating the opening of the cartridge." Pothier, like Becker, gave absolutely no thought whatever to the removal of any of the critical, decay causing, atmospheric elements entrapped within his sealed coffin.

All of the above cited patents, in addition to numerous other unidentified patents not mentioned herein, for caskets, coffins, and similar type burial containers, all suffer from a number of major disadvantages. Most specifically, the prior art patents:

(a) Fail to provide an attractive, serviceable, and relatively inexpensive type of burial container which will prevent/retard decomposition of the human and/or animal remains for up to 100 or more years.

(b) Fail to provide a burial type vehicle/container which will withstand the rigors of under-earth type burial conditions for up to 100 or more years.

(c) Fail to preserve the physical appearance/condition of deceased very important persons, such as Presidents, famous military leaders, and religious figures, so that future generations will be able to see their preserved busts, rather than just photographs and/or paintings.

OBJECTS AND ADVANTAGES

Accordingly, besides the objects and advantages of the burial capsule described in my above patent, several objects and advantages of the present invention are:

(a) to provide a burial capsule which will preserve and protect the human and/or animal remains which have been enbalmed and/or other wise immunized from the ravages of decay and decomposition for up to 100 or more years;

(b) to provide an extremely compact burial capsule which will permit the deposition of from one (1) to four (4) units, on the horizontal plane, within the confines of just one (1) single cemetery grave plot;

(c) to provide a burial capsule which will be extremely economical to manufacture, thereby resulting in a very substantial savings to the surviving family members;

(d) to provide a burial capsule which can be made from either a transparent or opaque material, thereby permitting the viewing of deceased loved ones, and/or Very Important Persons, at selected times for up to 100 or more years after the death had occurred;

(e) to provide an inexpensive, compact burial unit which may be inserted within the confines of an extremely expensive rental casket for viewing, prior to burial;

(f) to provide Peace and Tranquility to all living persons, by granting them the positive knowledge that, after they die, their own bodies will remain intact, essentially unaffected by the ravages of decay and decomposition, until long after all of their immediate loved ones have also died;

(g) to provide a compact, cocoon type burial container from which essentially all moisture and other types of contaminants, which contribute to or cause decomposition and/or decay of human and/or animal remains, can be removed or sterilized after the remains have been encased therein, thereby permitting the burial of individuals without the necessity of embalment!

(h) to provide a very small, compact, and extremely sturdy vehicle/container, wherein the human and/or animal corpse/remains, or any other type of desired items may be encapsulated for any desired purpose; most specifically the assembled, evacuated and sealed capsule will self-contain any and all types of infectious diseases or other types of contaminants which may have been present within the items or matter deposited therein.

(i) to provide a compact, sturdy burial capsule which may be utilized for the safe deposition, storage, and/or shipment of large quantities of human corpses, such as would be involved in times of war, major epidemics, and other types of local, national, and/or international disasters; whereas the vast quantities of capsules so involved could be compactly placed into any type of conventional racks or holding devices for temporary or long term storage, or shipment to any desired locations, via air, land or sea procedures.

Further objects and advantages are to provide a compact sealed capsule type of casket which, when fitted with the typical Anti-Flotation Adapter, may be buried in extremely low lying geographical areas without fear or concern that the units will float to the cemetery surface in later years. Still further objects and advantages will become apparent from a consideration of the ensuing description and drawings.

DRAWING FIGURES

FIG. 1 is an exploded view of two (2) identical segments, Part 1.A, the Base (Nesting) segment, and Part 1.B, the Cover segment, containing a half-moon shaped void at each end with three (3) component parts;

Female Reducer Bushing 2; Hose Adapter 3; and Male Plug 4

FIG. 2 is a side-view drawing of the completely assembled and sealed Burial Capsule, on the elevation plane, with cross-reference lines A—A Female Reducer Bushings 2; Hose Adapters 3; Vacuum Means 5; Inert Gas Means 6; and the fully assembled Burial Capsule 1. The horizontal line, which extends longitudinally through the center of the Burial Capsule, represents the chemical weldment zone, where parts 1 and 2 have been chemically welded together to become one (1) homogeneous, uniform chemical material purposes.

FIG. 3 is a cross-sectional view of the assembled and sealed Burial Capsule, taken at point A—A in FIG. 2 The chemical weld areas are not seen in this view because there is no physical distinction between the basis. Lines C—C refer to the representative height/depth of Parts 1.A and 1.B.

REFERENCE NUMERALS IN DRAWINGS

1 Burial Capsule after assembly and sealing
1.A Base (Nesting) segment of capsule
1.B Cover Segment of capsule
1.C Half-Moon shaped void
1.D Chemical weld joint around entire circumference
2 Female Reducer Bushing
3 Hose Adapter
4 Male Plug
5 Vacuum means (typical type envisioned)
6 Inert gas means

DESCRIPTION OF THE PREFERRED EMBODIMENTS—FIGS. 1 to 3

A typical embodiment of the Burial Capsule of the present invention is illustrated in FIG. 1 (Exploded view), FIG. 2

(Side view), and FIG. 3 (Section A—A view). The invention is comprised of two (2) identical segments 1.A and 1.B, which shall be available in various dimensions, so as to provide a convex, elongated, cylindrically shaped part, containing rounded ends, and a concentric center, which are designed to align and interface perfectly, after deposition of the desired items therein. The Capsule 1 may be chemically welded to form a sealed cocoon like vessel, capable of receiving an inert, gaseous atmosphere therewithin and retaining it indefinitely.

The preferred embodiment, the basic capsule, Parts 1.A and 1.B, are each made from a high strength, corrosion-resistant, Thermoplastic type of material, such as Lucite, Chlorinated Polyvinyl Chloride (PVC), or similar type material, which will withstand the rigors of underground exposure burial conditions for up to 100 or more years. These and similar types of satisfactory materials are as listed within the *Modern Plastics Encyclopedia*, Volume 68, Number 11, may be utilized.

These identical parts 1.A and 1.B may be thermoformed to the desired configuration and dimensions via any applicable, satisfactory thermoforming methodology, such as straight vacuum forming, mechanical drawing, or straight forming. These and other similar types of procedures are more fully described in the book *Plastics Technology*, by Robert V. Milby, published by the McGraw Hill Book Company, and other authoritative technical sources.

The basic parts 1.A and 1.B are typically 1.83 meters long, 0.63 meters wide, and 0.27 meters deep at the center most point. The nominal material thickness shall be approximately 1.3 millimeters. However, it is envisioned that the Burial Capsules will be provided in several sizes, so as to accommodate corpse sizes ranging from very small to very large. The actual controlling factor which will determine the maximum and minimum linear and width dimensions produced, shall be that the parts shall fit easily within the confines of standard size caskets, which are currently stocked within todays market places, such as Funeral Homes, and Mortuaries.

The semicircular openings 1.C, located in the center of each short end area of Parts 1.A and 1.B, may be accomplished by any standard, conventional methodology desired. The preferred method would be by physically cutting, or reaming procedures, to remove the unwanted basic material while it is still hot, immediately upon completion of the thermoforming phase of the operation. Other alternative methods would include mechanical drilling procedures, to create the entire intake and exhaust apertures in a single operation, after the corpse containing parts 1.A and 1.B have been properly married together, so as to form the cocoon type Burial Capsule shown in FIG. 2. Each of the two (2) holes so provided shall be of the appropriate dimensions so as to readily accept the Female Reducer Bushings 2, which will typically possess an outside diameter of approximately 2.5 to 4.0 millimeters.

A typical embodiment of the Base (Nesting) segment 1.A is to receive (1) a sponge, foam rubber, or similar type insert material (not shown), which will readily conform to the curvatures of a corpse when installed thereon; (2) a suitable, attractive coffin liner type of material, and (3) a matching pillow, as currently utilized within present day caskets. The properly embalmed and/or as otherwise prepared corpse shall be placed onto these materials, and the thus prepared 1.A segment presented for the final corpse-viewing phase of the burial ceremony. The thus prepared 1.A segment may either be displayed for viewing by loved ones as (a) a single unit, or (b) it may be inserted into an attractive casket, rented for display and viewing purposes only.

Upon completion of the final viewing phase of the funeral ceremony, the corpse containing Part 1.A shall be removed from within the rental casket, if utilized, and placed onto an appropriate flat, level surface. The flat, interfacing, i.e. mating surfaces, on both parts 1.A and 1.B, shall be uniformly coated with a copious amount of a compatible sealing material (not shown), as recommended by the Capsule manufacturer. Immediately after the sealing material has been applied, Part 1.B shall be inverted, and the treated flat surface lowered directly onto, and in complete alignment with, the matching flat surface of Part 1.A, so as to form one (1) unitary, cocoon type Burial Capsule unit, as seen in FIG. 2. The aligned and joined parts MUST NOT BE MOVED, or disturbed in any way for a minimum of ten (10) minutes. This undisturbed dwell time is mandatory, to assure that a satisfactory and complete curing action has been accomplished, and that the two (2) segments have been chemically welded together. The integrity of the entire chemically welded joint shall be ascertained via standard Non-Destructive Inspection (NDI) procedures, to include, but not limited to, visable and/or fluorescent penetrant (PT) and radiographic (RT) methodologies.

A standard Female Reducer Bushing 2, manufactured from a compatible material, and of the appropriate diameter as to fit properly within the Intake and Exhaust apertures (not shown), shall be coated on the outside diameter (O.D.) surface area, with a copious amount of the compatible sealer cement. A thus prepared Reducer Bushing 2 shall immediately be inserted into each of the two (2) Apertures located at opposite ends of the Capsule 1, so as to accomplish secure, leak proof mating all around. The properly installed Reducer Bushings 2 shall not be disturbed for a minimum of five (5) minutes. Either end of the Burial Capsule 1 may be utilized as the Intake end and the other end as the exhaust end of any Capsule 1 unit.

A standard Hose Adapter 3, manufactured from an appropriate Nylon or plastic type material, shall be temporarily installed within each of the Reducer Bushing 2 openings. A cylinder of an appropriate inert gas (6), such as Argon (A), Helium (H) or other applicable gas as listed within the Periodic Table of the Elements, Group I.A, shall be temporarily connected, via appropriate hoses and hose connections, to the Intake Hose Adapter 3. The cylinder valve shall be placed into the "OFF" position.

An appropriate Vacuum Pump (5) shall be attached to the Exhaust Hose Adapter 3, and the pump operated for a minimum of fifteen (15) minutes, or as recommended by the pump manufacturer, so as to completely evacuate most of the retained chemicals, moisture, and other foreign materials from within the sealed burial Capsule 1.

The Inert Gas cylinder valve shall be placed in the "OPEN" position for a minimum of ten (10) minutes prior to turning the Vacuum Pump valve to the "OFF" position. This action thus assures that the Burial Capsule 1 is completely charged with the Inert Gas medium. After the required Vacuum Pump operational time has been completed, the pump shall be turned off, and removed from the area.

The Exhaust Hose Adapter 3 shall then be removed from within the Female Reducer Bushing 2. With the Gas Cylinder valve still in the "OPEN" position, the threaded area on one (1) Male Plug 4 shall be uniformly covered with a copious amount of the proper sealing cement material, and immediately screwed securely into the Female Reducer Bushing 2 opening.

After the Gas Cylinder valve has remained in the "OPEN" position for a minimum of five (5) minutes after the Exhaust port hole has been secured, the valve shall be turned into the "OFF" position, and remove the cylinder from the immediate area. The Intake Hose Adapter 3 shall the be removed from within the Female Reducer Bushing 2. Promptly apply a copious amount of the appropriate sealing cement material onto the threaded area of a Male Plug 4, and immediately screw this plug into the Female Reducer Bushing 2 opening just vacated. This action concludes the gas charging and capsule sealing procedure, and the corpse containing Burial Capsule 1 is now ready for burial within an appropriate cemetery plot.

The required Female Reducer Bushing 2, Hose Adapters 3, and Male Plugs 4 are standard, off-the-shelf type items. They are readily available in plastic materials which are compatible with the materials which will be utilized to make the basic Burial Capsule parts 1.A and 1.B. These type items are manufactured by numerous sources, such as (1) R & G Sloane, 7777 Sloane Drive, Little Rock, Ark. 72206, (2) Mojak Plastic Manufacturing, Inc., Vernon, Calif. 90458, and other unidentified manufacturers too numerous to list within this instrument.

From the description above, a number of distinct advantages of my Burial Capsule 1 invention become evident:

(a) The total utilization of only an ultra high strength, plastic type material, which is essentially unaffected by the ravages of long-time exposure to the underground environment conditions, and high tensional and/or compressive stresses, will provide an ultra strong and durable storage vehicle, which, in turn, will provide the ultimate, unparalleled protection possible to any organic and/or inorganic matter contained therein, i.e., such as the human corpse, or other ultra-valuable items.

(b) The methodology utilized for exhausting the maximum amount of entrapped contaminants possible from within the sealed Capsule 1 by (1) first drawing a strong vacuum on the sealed Capsule 1, then (2) introducing an inert gas into the Capsule 1 interior, (3) to disconnect the vacuum system, and Hose Adapter 3, while the Capsule 1 is still being pressurized with the incoming inert gas medium, then (4) inserting a Male Plug 4, with the threaded area copiously coated with the appropriate cement/sealer material into the vacated Reducer Bushing 2 opening, therewith completely sealing the Burial Capsule 1 while it contains the maximum possible inert gas charge.

(c) The introduction, and indefinite retention, of a positive pressurized, inert gas medium, within the confines of the ultra strong Burial Capsule 1 produced by this invention, clearly provides a hermetically sealed, protected environment, which will protect the encapsulated corpse, or other items contained therein, from the ravages of decay and decomposition indefinitely.

(d) The utilization of a transparent material, such as Lucite, for the construction of the Burial Capsule 1, as cited within this invention, will protect the human body encased therein from the ravages of time, and still maintain the original physical appearance of the corpse, so that the bust of any desired Very Important Person could be viewed through the transparent Capsule material by yet unborn generations of mankind.

(e) Utilization of this Burial Capsule 1 invention will effectively eliminate the necessity that a bereaved family must purchase an expensive, ornate casket for the display and ultimate burial of their loved ones; whereas, by utilization of this Burial Capsule 1 invention, the most expensive of caskets may be rented, at a very nominal, reasonable fee for only the few days necessary for display and viewing, with the corpse nested within the Burial Capsule part 1.A installed therein, after which the Capsule part 1.A containing the corpse may be removed from within that casket, the casket returned to the rental source, and the corpse processed and buried within the Burial Capsule 1 as described herein.

(f) Utilization of this Burial Capsule 1 invention will eliminate the necessity that a burial vault be purchased to contain the casket, under the pseudo belief that the purchase of such would provide long-time protection to the casket and the corpse contained therein; whereas, this Burial Capsule 1 invention will provide the very maximum protection possible, as a self-contained unit, thereby eliminating the need for a vault.

(g) The minimum sized, hermetically sealed, long-time environmentally resistant Burial Capsule 1 will effectively protect the buried corpse contained therein for up to 100 years or more, thereby making it possible, logical and practicable that three (3) or more Burial Capsules 1 should be buried on the horizontal plane within one single cemetery burial plot, thereby providing the buyers with a monetary savings of sixty-six (66) percent.

(h) Utilization of this Burial Capsule invention will bring great and lasting mental peace and tranquillity to untold millions of people who lose loved ones, by their knowing that their departed person's physical body will remain intact, essentially unaffected by the ravages of decay and decomposition, for 100 years or more.

Operations: FIGS. 1, 2, 3

The first stage and manner of using the Burial Capsule 1 to receive a human corpse is essentially as that for using a standard current day casket. Namely, the interior of the Part 1.A base segment of the Burial Capsule 1 is adorned with adequate cushioning material, which is subsequently covered with an attractive liner material, and a small pillow is added to support the head. The corpse is processed, dressed in the desired attire, and then placed onto these materials within the Part 1.A Capsule Base. At the option of the bereaved family members, this Capsule Part 1.A containing the corpse may either be inserted within the confines of an ornate rental casket for viewing during the open-casket phase of the ceremony, or the Capsule Part 1.A may be used alone (FIG. 1,2).

The corpse containing Capsule 1.A may be readily extracted from within the confines of the rental casket via any conventional methodology such as a simple fabric, or fiberglass, type of sling arrangement, etc.

To properly close the Burial Capsule, after the viewing phase has been concluded, the flat interfacing surfaces of both Parts 1.A and 1.B are coated with a copious amount of the appropriate sealing cement material (not shown), Part 1.B inverted, and the flat surface area placed directly onto the matching flat surface area located on Part 1.A, so as to achieve a uniform fit all around. The two (2) segments of the Burial Capsule unit will therewith become one unit, completely married together by the resulting gravitational pressure being exerted thereon, plus the chemical welding action between the interfacing surfaces of Parts 1.A and 1.B. The complete and final marriage of Parts 1.A and 1.B will be completed within approximately ten (10) minutes after the Parts are combined (FIGS. 2,3).

To properly insert the Female Reducer Bushings 2 permanently and securely within the Intake and Exhaust openings, as seen in FIGS. 1 and 2, the outside diameter (O.D.) surface areas shall be coated with a copious amount of the proper sealing cement, and immediately inserted into the appropriate hole, using a "hands only, alternating twisting direction" technique, so as to assure that the entire surface area of each Reducing Bushing 2 becomes fully inserted and chemically welded to the basis capsule material.

To temporarily attach the required Inert Gas means (6) and the vacuum means (5), one must first screw a Hose Adapter 3 into the exposed female threads within each of the two (2) Reducer Bushings 2. The required attachment hose and hose connections shall be provided by the sources which provide the Gas Cylinders and the Vacuum Pump. The hose connections are simply connected to the Hose Adapter 3 fittings, and the Vacuum Pump operated in accordance with the instructions provided by the manufacturer, for the required amount of time as specified herein above. The Inert Gas cylinder is likewise operated in accordance with the instructions provided by the manufacturer, and as specified herein above.

Upon completion of the Exhaustion-Charging phase, the Hose Adapters 3 shall be removed from within the Female Reducer Bushings 2. The threaded area on two (2) Male Plugs 4 shall be fully coated with a copious amount of the appropriate sealing cement, and immediately screwed firmly and fully into the female openings of the two (2) Female Reducer Bushings 2.

The thus prepared Burial Capsule 1 weldment quality shall be ascertained via standard Non-Destructive Inspection (NDI) procedures, to include visable and/or fluoroscent penetrant (PT) and radiographic (RT) methodologies, as a minimum, and then physically moved to the prepared cemetery burial plot. Because of the special construction design, and the type of material utilized in the construction of the Burial Capsule 1, the requirement for a Vault has been eliminated. The Burial Capsule may be placed directly onto the excavation bottom, and the grave cavity refilled as necessary.

Summary, Ramifications, and Scope

Accordingly, the reader will see that the Burial Capsule 1 of this invention can be used to bury human and/or small animal remains, and/or extremely important and valuable materials or documents, and to rest assured that all such items will be fully protected from the ravages of decay and decomposition for up to 100, or more, years. Likewise, the reader can see that the minimal size, and the extreme strength of these Burial Capsules 1, will provide a very significant and substantial reduction in the costs associated with the burial of a loved one. Specific advantages and monetary savings associated with this invention are:

- it permits the Cost for production of burial capsules to be minimized, by the use of mass production techniques of only one (1) part, i.e., Part 1.A which requires only one (1) molding operation;
- it permits the bereaved family members to have their deceased loved ones corpse displayed in the most expensive of caskets, via rental procedures, at minimal cost;
- it permits the corpse, or other items, to be contained within an extremely strong and durable container, made from materials which are very corrosion resistant, and immune to the usually destructive, long-time exposure to under-ground stresses and adverse environmental conditions;
- it permits the corpse to be encapsulated within an inert gaseous medium, essentially void of all contaminants, so as to virtually arrest, and/or completely prevent further decay and decomposition actions on the contents contained within the Burial Capsule;
- it permits the burial of a loved one without the necessity of purchasing an expensive vault, as the Burial Capsule is not affected by underground environmental conditions;
- it permits the burial of multiple Burial Capsule units to be accomplished within one (1) single cemetery plot, one (1) directly above the other, on the horizontal plane, thereby substantially reducing the cost for purchasing cemetery burial plots to only one (1) plot for every three (3) or four (4) family members;
- it permits the burial of corpses within extremely low-lying geographical areas, via the utilization of the optional Anti-Flotation Adapter, without the fear of such items floating to the surface at some future date;
- it permits the corpses of Very Important Persons, such as ex-Presidents, Kings, Queens, military heroes, etc., to be buried in a mausoleum, within a transparent type material Burial Capsule, and their bodies preserved indefinitely, so that they may be seen by numerous generations of men yet to be born;
- it permits the immediate burial of corpses—without the need for embalment—thereby eliminating the extremely long periods of delays between death and burial, which are currently experienced by members of the Jewish faith, whereas their religion forbids that bodies be embalmed, and, consequently, burials are delayed for long periods of time;
- it permits subsequent re-opening of the Capsule unit in the event of a compelling requirement, via the utilization of a standard circular type saw to make a circumferential cut approximately five (5) millimeters above the current chemical weldment bead;
- it permits the thus opened Burial Capsule unit to be re-assembled, re-chemically welded, contaminates re-extracted from within the sealed unit, and the interior re-charged with inert gas, by merely re-drilling the standard sized void on each end of the Capsule, installing new component parts, i.e., the Reducer Bushing, Hose Adapters and Male Plugs, and processing in accordance with the prior procedure as was utilized for the original assembly.

Additional Ramifications

Although the description above contains many specifications, these should not be construed as limiting the scope of the invention, but as merely providing illustrations of some of the presently preferred embodiments of this invention. For example, the Burial Capsule can have other shapes, such as triangular, rectangular, etc.; the Intake and Exhaust port holes (voids) can be placed in other locations; the flat interfacing surfaces utilized for joining the two (2) segments together may be a tongue and groove configuration, additional and/or alternative procedures for accomplishing sterilization of the encapsulated burial capsule interior may be utilized, etc.

The typical Anti-Flotation Adapter can have other shapes and dimensions, may be made from different types of material, and contain different types of interlocking mechanisms; the legs can have different design characteristics to effect penetration and/or locking within the substrate material, etc.

Thus, the scope of the invention should be determined by the appended claims, rather than by the examples given.

Having thus described the invention, what is claimed is:

1. A burial capsule with anti-decay system for containment of a human corpse, small animal carcass, or other cherished and valuable items within a pressurized, inert gas atmosphere which will protect said items from the effects of decay and decomposition, said capsule consisting of:

two (2) identical, pre-formed, rigid material segments of an appropriate plastic composition, each of said segments including an elongated continuous convex segment adapted to be chemically welded with the other segment forming a cylindrical shaped capsule;

a plurality of small diameter apertures which penetrate through said capsule wall;

a plurality of female reducer means, chemically welded into said apertures;

a plurality of hose adapter means for temporary insertion into said female reducer means; and a plurality of male plug means chemically weldable into said female reducer means, after the removal of said hose adapter means has been completed, to effectively and permanently seal said burial capsule.

2. A burial capsule as in claim 1, wherein said female reducer means including a basis, female threaded receptacle to facilitate the temporary attachment of said hose adapter means, said hose adapter means adapted to connect to a remotely located vacuum pump means, and an inert gas means.

3. A burial capsule as in claim 1, wherein said capsule consist of a single, homogenous chemical material, which contains an inert gas atmosphere to prevent and/or retard decay and decomposition of items contained therein.

* * * * *